United States Patent [19]

Bellani et al.

[11] Patent Number: 5,696,300
[45] Date of Patent: Dec. 9, 1997

[54] PROPOFOL PURIFICATION

[75] Inventors: Piero Bellani, Rho; Maurizio Velati, Pavia, both of Italy

[73] Assignee: Archimica SPA, Origgio, Italy

[21] Appl. No.: 591,600

[22] PCT Filed: Jun. 28, 1995

[86] PCT No.: PCT/EP95/02520

§ 371 Date: Feb. 9, 1996

§ 102(e) Date: Feb. 9, 1996

[87] PCT Pub. No.: WO96/01243

PCT Pub. Date: Jan. 18, 1996

[30] Foreign Application Priority Data

Jul. 1, 1994 [IT] Italy ................... MI94A1377

[51] Int. Cl.$^6$ ................... C07C 37/68
[52] U.S. Cl. ................... 568/749; 568/750
[58] Field of Search ................... 568/749, 750

[56] References Cited

U.S. PATENT DOCUMENTS 3,517,072 6/1970 Moroni et al. .
3,630,855 12/1971 Turbun et al. .
3,772,394 11/1973 Milnes .
5,175,376 12/1992 Nieminen et al. .................. 568/781

FOREIGN PATENT DOCUMENTS 0511947 11/1992 European Pat. Off. .
855489 11/1960 United Kingdom .

OTHER PUBLICATIONS

Purification of Laboratory Chemicals, Perrin et al, p. 560, Paragraph Labeled "Phenols" 1980.

J. Chem. Soc., Perkin Transactions 1, No. 12, 3229–3231 (1988).

Primary Examiner—Samuel Barts
Attorney, Agent, or Firm—Michael N. Meller

[57] ABSTRACT

Propofol is purified by reaction of the raw 2,6-diisopropylphenol with an alkaline agent, by isolation of the alkaline metal salt and by neutralization thereof. There is thus obtained a propofol having a purity of at least 99.90%.

9 Claims, No Drawings

PROPOFOL PURIFICATION

This application is a 371 of PCT/EP95/02520 filed Jun. 28, 1995.

Propofol, or 2,6-diisopropylphenol, having the formula

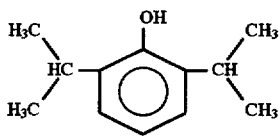

is a well known compound which is largely produced for its use as an antioxydant. Processes for its preparation are described, for instance, in U.S. Pat. No. 2,831,898, U.S. Pat. No. 4,103,096, U.S. Pat. No. 4,208,537, U.S. Pat. No. 4,275,248, U.S. Pat. No. 4,447,657, U.S. Pat. No. 4,538,009, U.S. Pat. No. 4,559,465, JP 62-209034 and SU 443,019. Its use as an anaesthetic for parenteral administration is described in U.S. Pat. No. 4,056,635 and such an use is become common in surgery.

Since propofol is administered by parenteral route, its purity degree must be very high and thus involves fractionated distillations which, on one side, need supplemental apparatus and, on the other side, involves a loss of active principle.

European patent application No. 551,947 discloses a method for the purification of propofol by fractionated crystallisation at very low temperature which, according to the disclosure of the cited document, allows the obtention of 60 g of propofol with a purity of at least 99.90% starting from 100 g of propofol having a purity degree of 99.7%.

It has now been found that a propofol with a pharmaceutical purity for parenteral administration may be obtained by conversion in one of its alkaline metal salt and by neutralization of pure salt thus isolated.

Thus, it is an object of the present invention to provide a process for the purification of propofol which comprises treating the raw product with a base of formula

wherein R is hydrogen or a straight or branched chain alkyl group, preferably a lower alkyl group of from 1 to 4 carbon atoms, R' is an alkaline or an alkaline-earth metal and n is one or two, depending upon the valence of the metal R', isolating the salt thus obtained and converting it into pure propofol by neutralization with an organic or inorganic acid, preferably with a mineral acid.

According to the process of the present invention, the salification of the phenolic hydroxy group is carried out by treatment with an alkaline agent such as sodium or potassium ($C_1$–$C_4$)alkanoate, for example sodium or potassium methylate or ethylate, sodium amide or such as sodium or potassium hydroxide. Preferably, sodium methylate is used.

The salt forming reaction is carried out in a polar solvent, preferably in an alcohol expecially when an alkaline metal alcoholate is used as an alkaline agent; furthermore, in this case, it is also preferable that the alcohol is the same as the employed alcoholate.

The reaction temperature is of 25°–50° C., preferably of 35°–45° C., and the alkaline metal salt thus obtained is isolated by evaporating the solvent, taking up the residue with an organic solvent wherein the salt of 2,6-diisopropylphenol (propofol) thus obtained is insoluble, and thoroughly washing this salt with the same solvent.

This solid product (the alkaline or alkaline-earth metal salt of 2,6-diisopropylphenol) thus obtained in a pure state is neutralized with an organic or inorganic acid and propofol is isolated by extraction, preferably with toluene, evaporation of the solvent and distillation at about $1.7 \times 10^3$ pascal.

The neutralization may be made with a mineral acid, such as hydrogen chloride in aqueous solution, or with an organic acid, such as methanesulfonic, formic or acetic acid.

According to a preferred feature, the raw propofol is treated with sodium methylate in methanol at a temperature of 35°–45° C. and, after distilling the solvent at about $2.6 \times 10^3$ pascal, the oily residue is taken up with toluene. In this solvent, the sodium 2,6-diisopropylphenate separates in a solid state whilst all the impurities remain dissolved. Thus, by filtration and washing with toluene, the still wet, pure sodium salt is isolated and neutralized with an aqueous solution of hydrogen chloride and pure propofol is isolated by extraction with toluene and distillation at 98°–100° C. and $1.7 \times 10^3$ pascal.

The chemical method, which takes advantage of the insolubility of the alkaline or alkaline-earth metal salt of propofol in the solvent which solubilizes the impurities, allows the recovering of the whole propofol which is present in the raw material and the obtention of a very pure propofol.

The following example illustrates the invention without, however, limiting it.

EXAMPLE 1

To 2.4 Kg of methanol, previously cooled to 10°–15° C., 380 g of sodium methylate are added, whereby maintaining the temperature constant by an appropriate cooling and by carrying out the addition portionwise. The solution thus obtained is heated to 35°–45° C. and 1.19 Kg of raw propofol (purity 97%) are added thereinto. The suspension thus obtained is kept under stirring for 30 minutes at 40°–50° C., then it is distilled at about $2.6 \times 10^3$ pascal up to a residue which is taken up with 3 Kg of toluene. There is obtained a suspension which is stirred for 30 minutes at 5°–10° C. The sodium 2,6-diisopropylphenate thus obtained is filtered and washed with anhydrous toluene until it becomes colourless. The product, still wet of toluene, is added to a solution of 1.3 Kg of 37% hydrochloric acid in 4.5 Kg of water and the propofol is extracted with 2.7 Kg of toluene at 20°–22° C., at a decidedly acid pH. The organic phase is washed with a 10% aqueous solution of sodium chloride, then it is distilled at about 60° C. and at about $2.6 \times 10^3$ pascal until an oil is obtained which, in its turn, is distilled under vacuum (about $1.7 \times 10^3$ pascal) by eliminating the fraction boiling at 60°–98° C. and recovering the product at 98°–100° C. Thus, there is obtained 1 Kg of pure propofol having the following characteristics:

appearance: colourless or yellowish oil;

purity; ≧99.90% (determined by HPLC);

residual solvents: ≦0.1% (determined by GLC).

We claim:

1. A process for the purification of 2,6-diisopropylphenol which comprises treating the raw 2,6-diisopropylphenol with a base of formula

wherein R is hydrogen or a straight or branched chain alkyl group, R' is an alkaline or an alkaline-earth metal and n is one or two, depending upon the valence of the metal R', isolating the salt thus obtained and converting it into pure propofol by neutralization with an organic or inorganic acid.

2. A process according to claim 1 wherein the base used has the formula

(RO)$_n$—R' in which R' is sodium or potassium, R is a lower alkyl group of from 1 to 4 carbon atoms and n is one.

3. A process according to claim 1 wherein sodium methylate is used as a base and the salification is carried out in methanol.

4. A process according to claim 1 wherein the neutralization is carried out with a mineral or organic acid.

5. A process according to claim 4 wherein said mineral acid is an aqueous solution of hydrochloric acid.

6. A process according to claim 4 wherein said organic acid is selected from the group consisting of methanesulfonic, formic and acetic acid.

7. A process according to claim 1, wherein the obtained alkaline or alkaline-earth metal 2,6-diisopropylphenate is washed with a solvent in which said salt is insoluble.

8. A process according to claim 7 wherein said solvent is toluene.

9. A process according to claim 1 wherein the isolation of the pure 2,6-diisopropylphenol is carried out by distillation at 98°–100° C. and the pressure of $1.7 \times 10^3$ pascal.

* * * * *